United States Patent
Schubert et al.

(10) Patent No.: US 9,125,601 B2
(45) Date of Patent: Sep. 8, 2015

(54) BACK NEEDLE

(75) Inventors: Jacob Boegh Schubert, Graested (DK); Thibaud Hofstätter, Elsingore (DK)

(73) Assignee: Novo Nordisk A/S, Bagsvaerd (DK)

( * ) Notice: Subject to any disclaimer, the term of this patent is extended or adjusted under 35 U.S.C. 154(b) by 1490 days.

(21) Appl. No.: 12/529,877

(22) PCT Filed: Mar. 7, 2008

(86) PCT No.: PCT/EP2008/001832
§ 371 (c)(1),
(2), (4) Date: Jan. 4, 2010

(87) PCT Pub. No.: WO2008/107199
PCT Pub. Date: Sep. 12, 2008

(65) Prior Publication Data
US 2010/0114035 A1  May 6, 2010

Related U.S. Application Data

(60) Provisional application No. 60/918,881, filed on Mar. 19, 2007.

(30) Foreign Application Priority Data

Mar. 7, 2007 (EP) .................... 07103675

(51) Int. Cl.
*A61M 5/00* (2006.01)
*A61B 5/15* (2006.01)
*A61M 5/32* (2006.01)

(52) U.S. Cl.
CPC .............. *A61B 5/1444* (2013.01); *A61M 5/321* (2013.01); *A61M 5/3271* (2013.01); *A61M 2005/3254* (2013.01)

(58) Field of Classification Search
CPC ................... A61M 2005/3254; A61M 5/2466; A61M 5/326; A61M 5/347
USPC ................. 604/206, 192–198, 110, 246–256, 604/533–284, 189
See application file for complete search history.

(56) References Cited

U.S. PATENT DOCUMENTS

| | | |
|---|---|---|
| 4,774,964 A | 10/1988 | Bonaldo |
| 5,336,200 A | 8/1994 | Streck et al. |
| 5,810,775 A | 9/1998 | Shaw |
| 5,941,857 A | 8/1999 | Nguyen et al. |
| 7,384,414 B1 * | 6/2008 | Marshall et al. ............. 604/198 |

FOREIGN PATENT DOCUMENTS

| | | |
|---|---|---|
| EP | 1449555 A1 | 8/2004 |
| EP | 1747789 | 1/2007 |
| JP | 11-155952 A | 6/1999 |
| JP | 2007-502156 A | 2/2007 |
| WO | WO 90/02515 | 3/1990 |
| WO | WO 92/20281 | 11/1992 |

(Continued)

*Primary Examiner* — Phillip Gray
(74) *Attorney, Agent, or Firm* — Novo Nordisk Inc

(57) ABSTRACT

A needle assembly for an injection device comprising a needle cannula which is mounted in a hub connectable to an injection device, and which needle assembly comprises a back needle. Further the needle assembly is provided with means which, when activated, prevents a user from physically contacting the back needle.

8 Claims, 8 Drawing Sheets

(56) References Cited

FOREIGN PATENT DOCUMENTS

| WO | 01/91837 A1 | 12/2001 |
| WO | WO 03/045480 | 6/2003 |
| WO | 2005/018722 A1 | 3/2005 |

\* cited by examiner

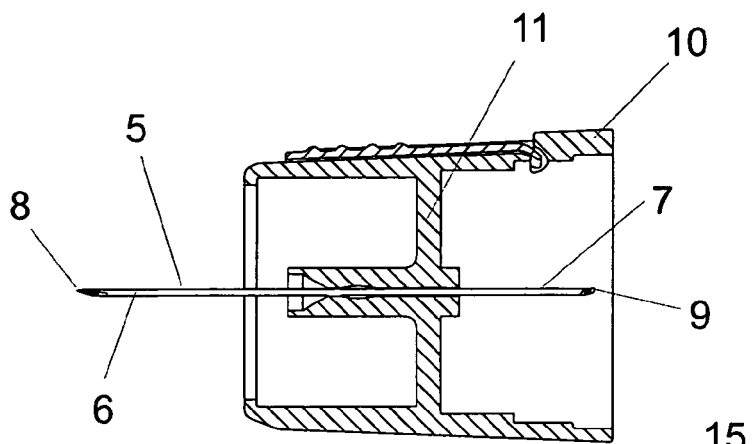
Fig 1A
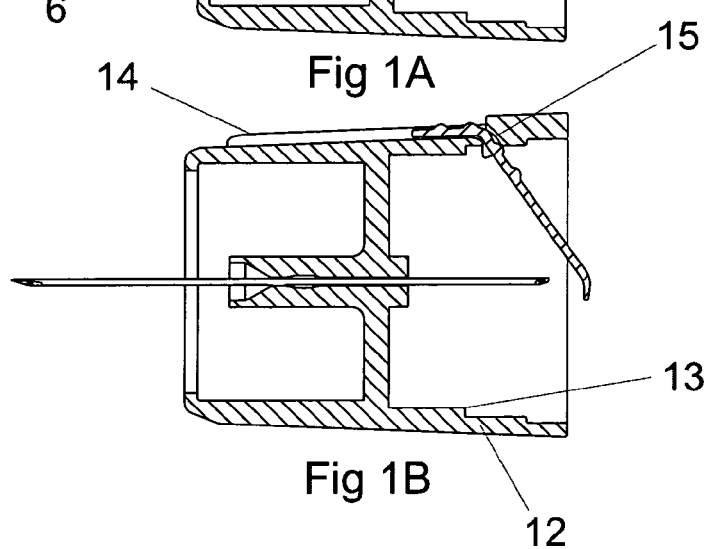
Fig 1B
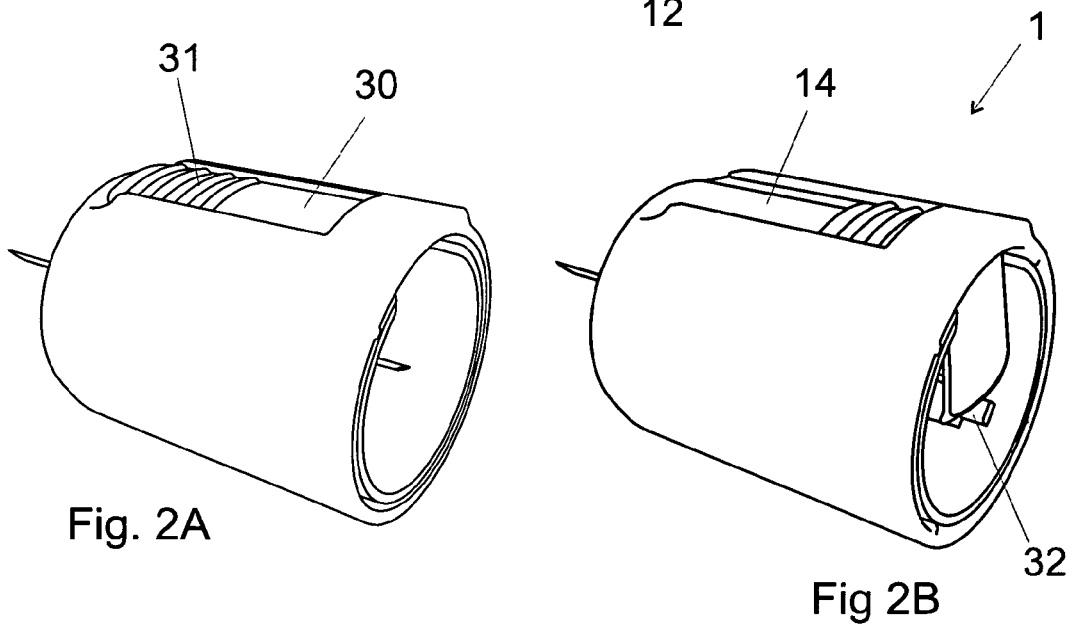
Fig. 2A
Fig 2B

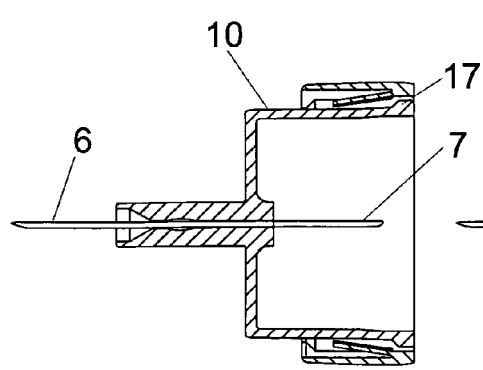 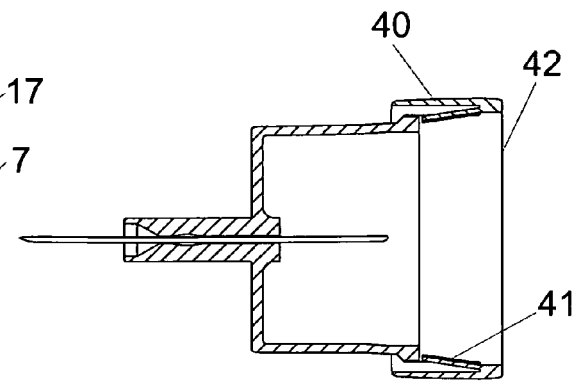
Fig. 4A                Fig. 4B
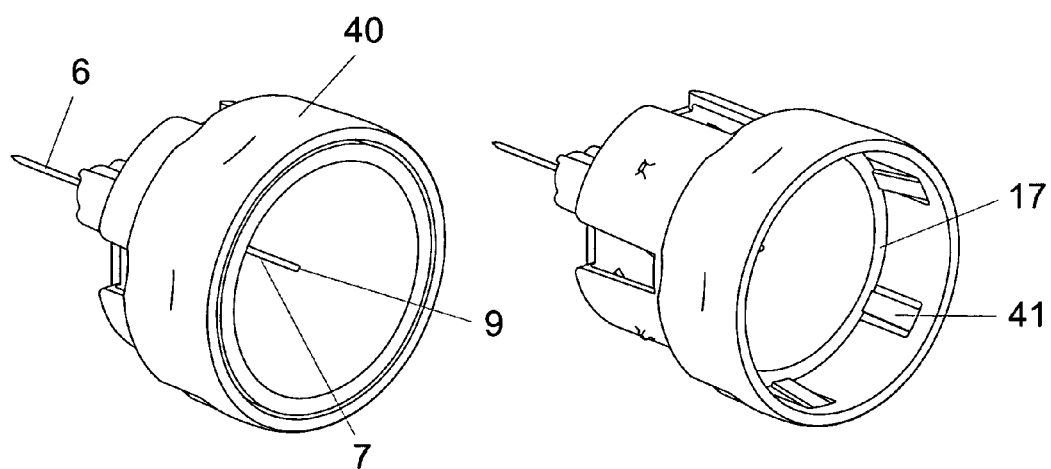
Fig. 5A                Fig 5B

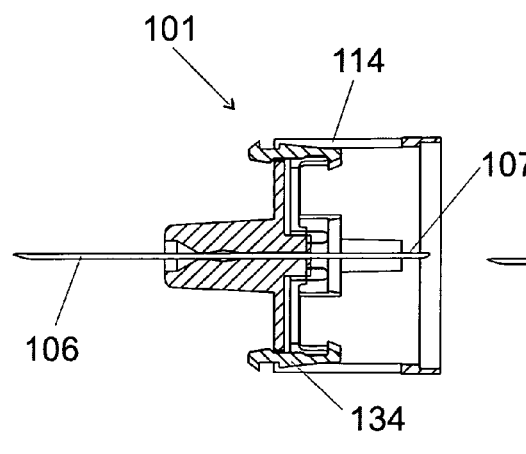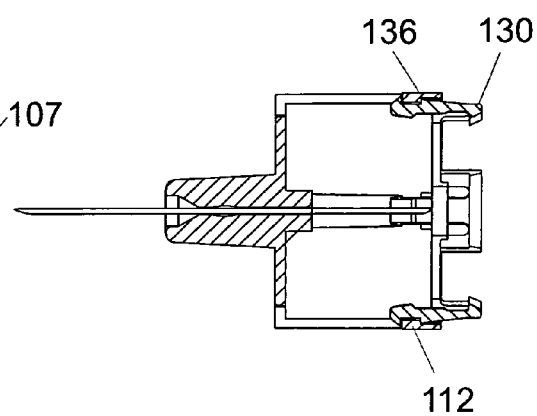
Fig. 10A                Fig. 10B
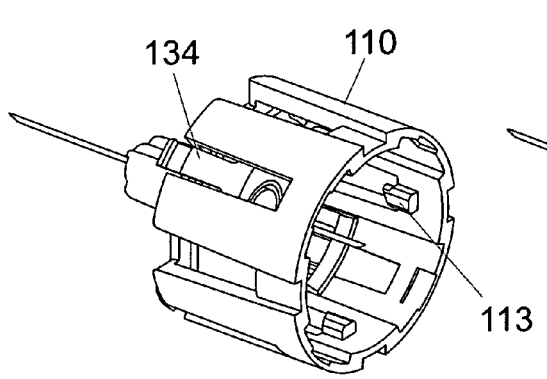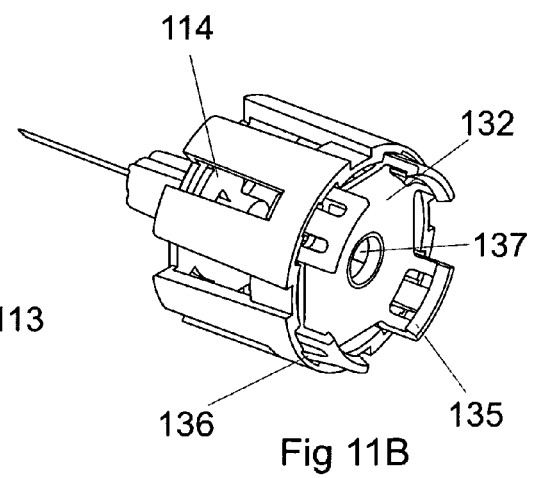
Fig. 11A                Fig 11B

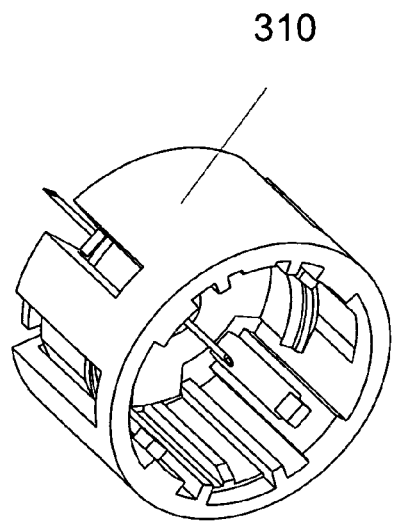
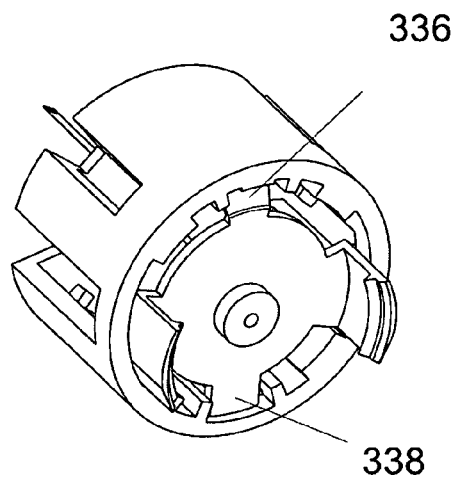
Fig. 14A          Fig. 14B
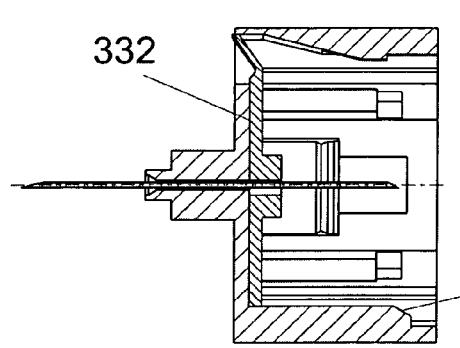
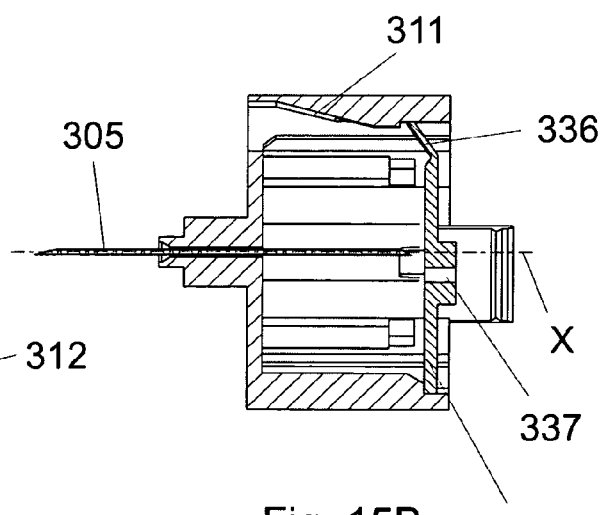
Fig. 15A          Fig. 15B

BACK NEEDLE

CROSS-REFERENCE TO RELATED APPLICATIONS

This application is a 35 U.S.C. §371 national stage application of International Patent Application PCT/EP2008/001832 (published as WO 2008/107199), filed Mar. 7, 2008, which claimed priority of European Patent Application 07103675.0, filed Mar. 7, 2007; this application further claims priority under 35 U.S.C. §119 of U.S. Provisional Application 60/918,881, filed Mar. 19, 2007.

THE TECHNICAL FIELD OF THE INVENTION

The invention relates to a double pointed needle assembly and especially to such needle assembly having a means protecting the user from accidental being injured by the back needle.

DESCRIPTION OF RELATED ART

Needle assemblies are commonly used to either inject substances into or extract substances out of human or animal bodies. Such needle assemblies are typically disposable and are discarded after use.

In some injection devices the liquid medicament to be injected is delivered in cartridges which are insertable in the injection device. Such cartridge comprises an ampoule often made from glass which at one end is closed by a rubber membrane and at the other end sealed by a movable rubber piston. The medicament is forced out through a conduit which is penetrated through the rubber membrane and into the ampoule by moving the piston forward inside the ampoule.

For the purpose of penetrating the rubber membrane double pointed needle assemblies has been developed. Such double pointed needle assembly is disclosed in European Patent No.: 1.449.555 and comprises a hub which is attachable to the injection device and a needle cannula having a distal part for penetrating the skin of a user and a proximal part for penetrating through the rubber membrane of the ampoule.

One problem presented by the disposal of a needle assembly, and indeed, by any handling of the needle assembly, is the potential risk of being injured by the sharp ends of the needle cannula. This is particular dangerous when following after the penetration of a patients skin since the needle cannula then may be contaminated and therefore capable of spreading diseases such as hepatitis and HIV. A great number of needle assemblies have been developed where the skin penetrating part of the needle cannula is concealed by a spring loaded and telescopically movable shield during the injection. One such safety needle assembly is described in WO 2001/91837, which is hereby incorporated by reference.

All though the part of the needle cannula that penetrates the rubber membrane is usually surrounded by the sleeve of the hub there is still a potential risk that people can physically contact this back needle and be accidentally infected.

One solution to this is disclosed in U.S. Pat. No. 5,941,857 which discloses a needle assembly which is provided with a separate needle shield that the user manually can place over the back part of the needle cannula after use.

Further a number of blood collection devices have been provided with back needle protection, e.g as described in U.S. Pat. No. 4,774,964 and in WO 92/20281.

However, these known solutions require the user to perform a manual operation which places the user at risk for accidental being injured by the sharp end of the needle.

Thus, there is a need for a double pointed needle assembly that can provide safety against accidental needle stick injuries in more situations.

DESCRIPTION OF THE INVENTION

It is an object of the present invention to provide a needle assembly having a shielded back needle which can be locked automatically.

In pen needles traditional used for injecting insulin or growth hormone, the back needle that penetrates into the cartridge is surrounded by the skirt of the hub carrying the connecting means. In the present invention additional means are be provided which prevents the user from physically contacting this so called back needle, thus protecting the user from contamination.

These means are formed as an element being movable from a first position to a second position, in which second position the means are lockable.

The movable element can have the form of a shield or plate and is preferably provided with means making it engageable with an injection device such that the shield or plate engages with the injection device when the needle assembly is attached to the injection device and is automatically pulled into the protection position by movement of the injection device as occurs when the needle assembly is dismounted from the injection device. In this way the shield or plate is automatically retracted into its locked position when the needle assembly is being removed from the injection device without the user has to perform any specific action.

The needle assembly can further be provided with means such as locking arms for irreversible locking the shield or plate in its retracted position.

DEFINITIONS

An "injection pen" is typically an injection apparatus having an oblong or elongated shape somewhat like a pen for writing. Although such pens usually have a tubular cross-section, they could easily have a different cross-section such as triangular, rectangular or square or any variation around these geometries.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

Correspondingly, the term "subcutaneous" injection is meant to encompass any method of transcutaneous delivery to a subject.

Further the term "injection needle" defines a piercing member adapted to penetrate the skin of a subject for the purpose of delivering or removing a liquid.

The term "Needle Cannula" is used to describe the actual conduit performing the penetration of the skin during injection. A needle cannula is usually made from a metallic material and connected to a hub to form an injection needle. A needle cannula could however also be made from a polymeric material or a glass material. The hub which carries the connecting means for connecting the injection needle to an injection apparatus is usually moulded from a suitable thermoplastic material.

"Cartridge" is the term used to describe the container containing the insulin. Cartridges are usually made from glass but could also moulded from any suitable polymer. A cartridge or ampoule is preferably sealed at one end by a pierceable membrane which can be pierced e.g. by an injection needle. The opposite end is closed by a plunger or piston made from rubber or a suitable polymer. The plunger or piston can be slidable moved inside the cartridge. The space between the pierceable membrane and the movable plunger holds the insulin which is pressed out as the plunger decreased the volume of the space holding the insulin.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which:

FIG. 1A-B Show a cross section of an example of a protected back needle.

FIG. 2A-B Show a three dimensional view of the needle assembly of FIG. 1A-B.

FIG. 4A-B Show a cross section of a hub enlargement.

FIG. 5A-B Show a three dimensional view of the needle assembly of FIG. 4A-B.

FIG. 10A-B Show a cross section of a different protected back needle.

FIG. 11A-B Show a three dimensional view of the needle assembly of FIG. 10A-B.

FIG. 14A-B Show a three dimensional view of an alternative back needle protection.

FIG. 15A-B Show a cross sectional view of the needle assembly of FIG. 14A-B.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

Figure 3A:
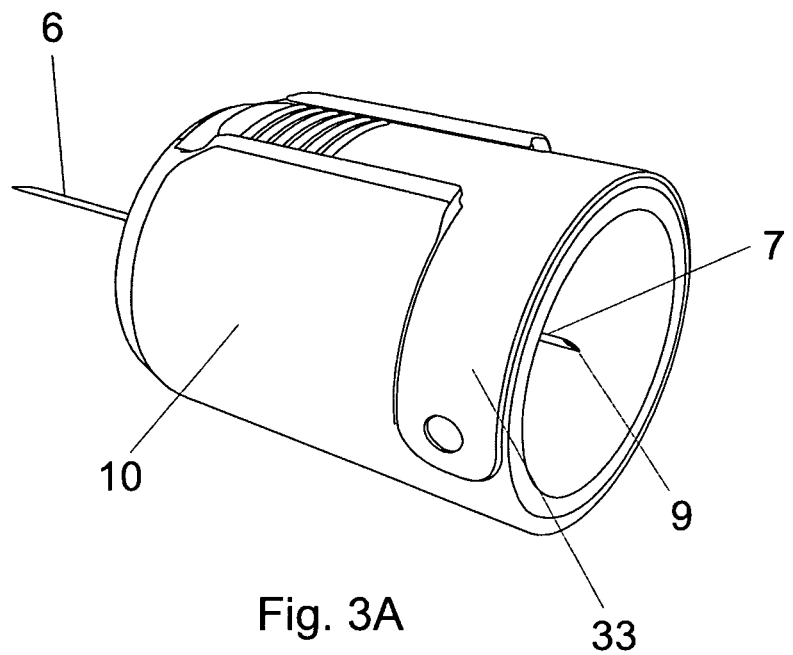
FIG. 3A-B Show a three dimensional view of an example of a protected back needle.

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the injection device carrying the injection needle whereas the term "proximal end" is meant to refer to the opposite end pointing away from the injection needle.

All though the needle assembly detailed in the following examples is disclosed without any protection of the distal part of the needle cannula it is evident that the disclosed back needle protection can be combined with almost any kind of fore needle protection e.g. the one described in European patent application No. 06-126970, which is hereby incorporated by reference.

Example 1

FIG. 1-2

FIGS. 1 and 2 discloses a needle assembly 1 comprising a needle cannula 5 attached to a hub 10.

The needle cannula 5 is a thin hollow metallic conduit having a first elongated part 6 with a first distal sharp end 8 and a second elongated part 7 with a second sharp proximal end 9. The distal end penetrates the skin of a user during injection and the opposite proximal end penetrates into a not shown container in an injection device when the needle assembly 1 is attached to the injection device.

The hub 10 which is usually moulded from a thermoplastic material comprises a base 11 to which the needle cannula 5 is attached e.g. by gluing. From the base 11 an annular sleeve 12 extends in the proximal direction. This annular sleeve 12 surrounds the second part 7 of the needle cannula 5 and is provided with connecting means 13 for connecting the needle assembly 1 to the injection device.

All though the second part 7 of the needle cannula 5 is surrounded by the annular sleeve 12 it is possible for a person to be injured by the sharp proximal end 9 when the needle assembly 1 is not attached to an injection device. In order to prevent this, the needle assembly 1 can be equipped with a shield 30. This shield 30 is preferably made from a material being softer than the hub 10 and is slidable positioned in a track 14 formed in the outside surface of the hub 10.

At one end the shield 30 can be provided with ribs 31 to provide a better grip for the fingers of the user and at the other end it can be provided with a needle covering element 32. The hub 10 is provided with an opening 15 guiding the shield 30 from the outside of the hub 10 to the inside once the shield 30 is moved in the proximal direction. This opening 15 in the hub 10 is located and angled in such way that the shield 30 slides into a position proximal of the sharp proximal end 9 of the needle cannula 5 when used.

In operation the user simply moves the shield 30 in the proximal direction after dismounting the needle assembly 1 following an injection by pushing on the ribs 31. This proximal movement forces the shield 30 though the opening 15 in the hub 10 and into a position covering the sharp proximal end 9 of the needle cannula 5.

Example 2

FIG. 3

Figure 3B:
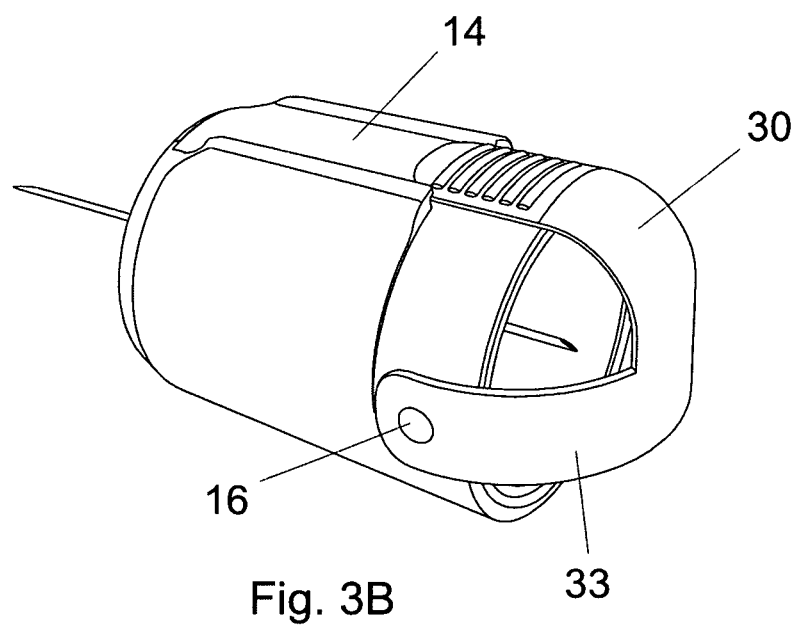

As shown in FIG. 3, the shield 30 can be formed with two hinges 33 which are attached to the hub 10 in two pivot points 16 as disclosed in FIG. 3. Once a user moves the shield 30 in the proximal direction the two hinges 33 rotates around the pivot points 16 and the shield 20 moves into a position covering the proximal end 9 of the needle cannula 5.

Alternatively the shield 30 can be moulded in one with the hub 10. If e.g. film hinges are provided at the engagement point with the hub 10 and at the hinges 33, the shield 30 would be able to fold into a locking position.

Example 3

FIG. 4-5

FIGS. 4 and 5 discloses a needle cannula 5 mounted in a hub 10. The hub 10 is further provided with a circular ring element 40 which surrounds the hub 10. The ring element 40 has a bore slightly larger than the diameter of the hub 10 and can be telescoped in a proximal direction over the hub 10.

When a user has removed the needle assembly 1 from the injection device following an injection, the user pulls the ring element 40 in the distal direction until the flexible arms 41 on the ring element 40 engages behind a peripheral protrusion 17 provided proximally on the hub 10. In this position, the ring element 40 is locked relatively to the hub 10. The distance from the proximal end 42 of the ring element 40 to the sharp end 9 of the proximal end 7 of the needle cannula 5 has thereby been increased making it nearly impossible for the user to physically contact the proximal sharp end 9 of the needle cannula 5.

Example 4

FIG. 6-7

Figure 6:
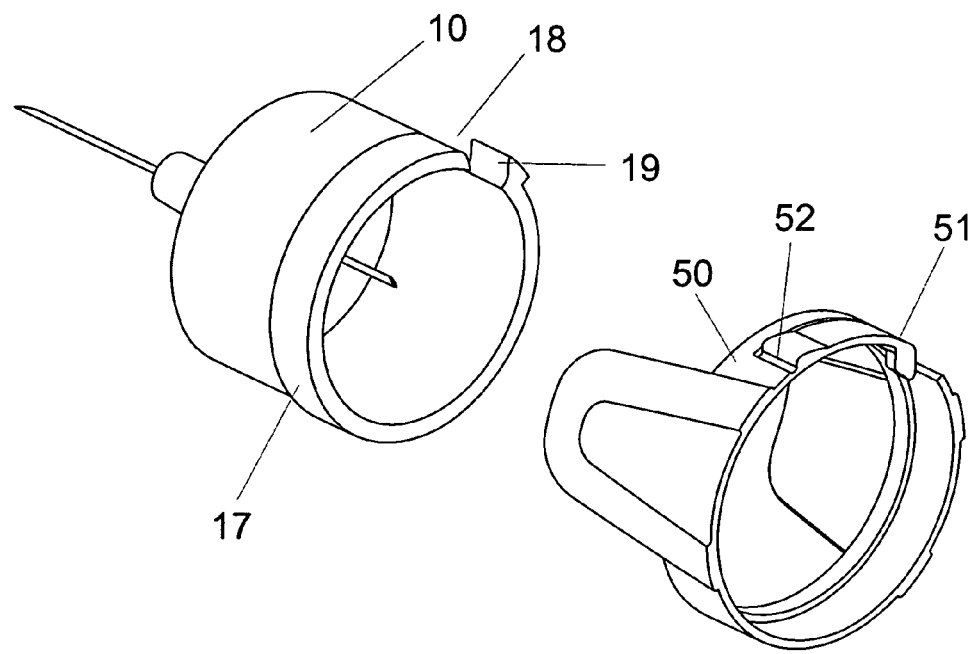
FIG. 6 Show an exploded view of another back needle protection.
Figures 7A, 7B:
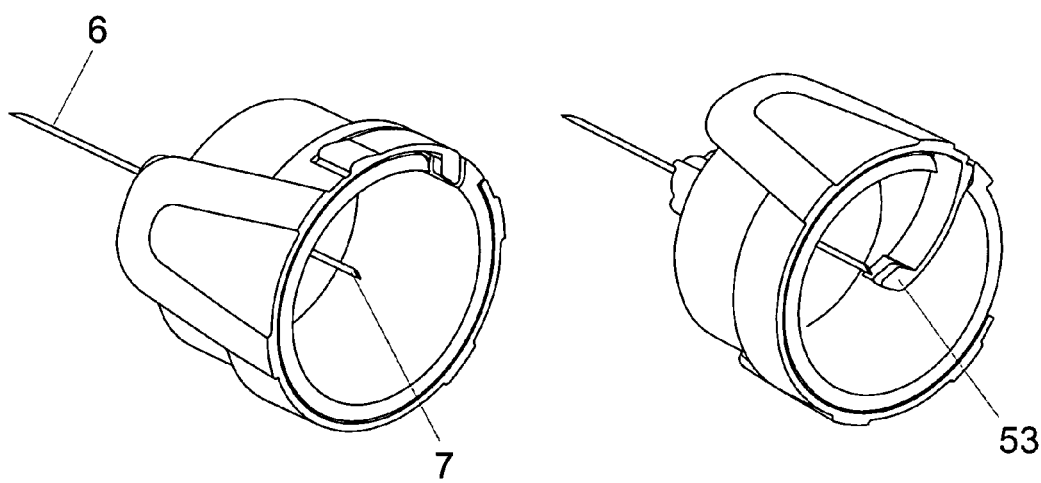
FIG. 7A-B Show a three dimensional view of the needle assembly of FIG. 7.

A different solution is disclosed in FIG. 6-7. The needle cannula 6 is mounted in the hub 10 which at its proximal end is provided with a peripheral protrusion 17. Further the hub 10 is provided with a slot 18 located in the annular sleeve 12 and interrupting the peripheral protrusion 17. The slot 18 is further provided with a steep angled surface 19 for guiding the shield arm 51.

A rotatable shield element 50 is provided on the hub 10. This rotatable shield element 50 has a shield arm 51 which is connected to the rotatable shield element 50 by a flexible film hinge 52 such that the shield arm 51 can flex. The shield arm 50 is at its free end provided with covering means 53 for covering the proximal end 9 of the needle cannula 5 when the shield arm 51 is in its locked position.

When a user rotates the shield element 50 relatively to the hub 10, the shield arm 51 is forced to flex due to its encounter with the steep surface 19 and the covering means 53 on the shield arm 51 is guided into a position proximal of the proximal end 9 of the needle cannula 5. The needle assembly 1 could further be provided with locking means e.g. a click mechanism arresting the shield arm 53 in the locked position or any other suitable locking system as could the needle assembly 1 be provided with more than one arm.

Example 5

FIG. 8-9

Figure 8:
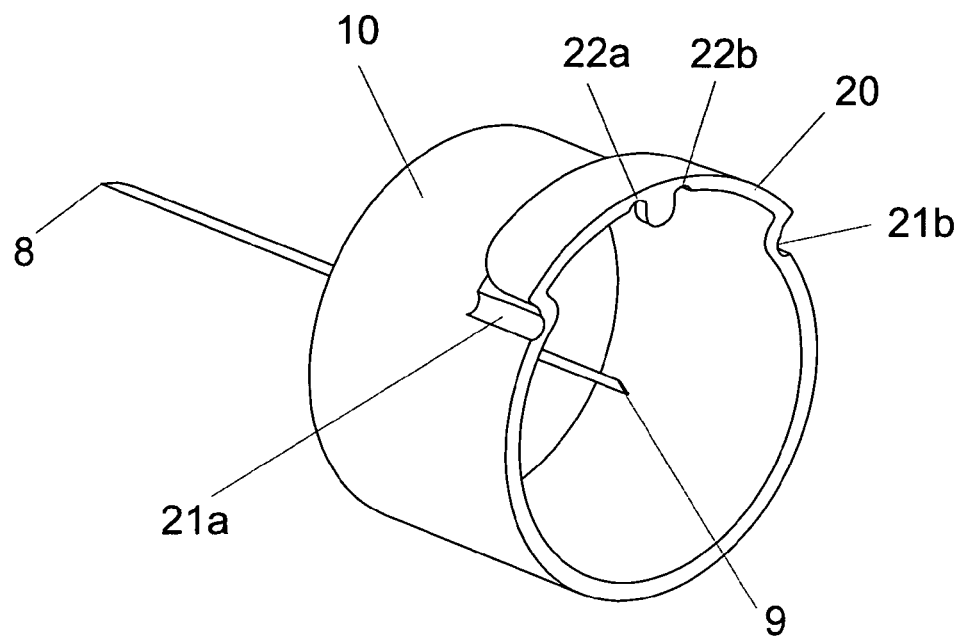
FIG. 8 Show a three dimensional view of a back needle protection.
Figure 9:
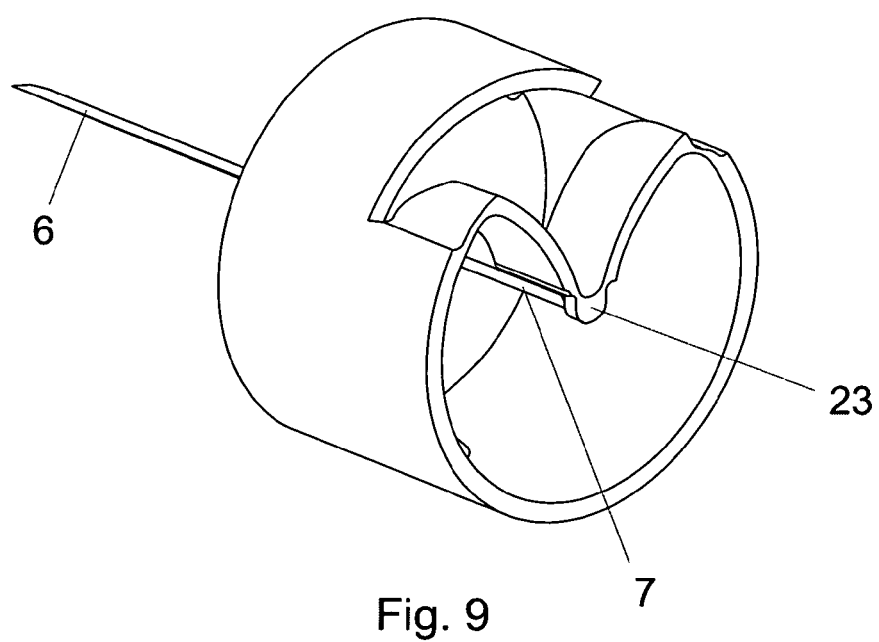
FIG. 9 Show a three dimensional view of the needle assembly of FIG. 8.

FIG. 8-9 discloses a solution where the hub 10 is provided with a flexible part 20 which is attached to the hub 10 by film hinges 21a,b. In the centre of the flexible part 20 a covering element 23 is provided which is surrounded by two additional film hinges 22a,b.

When a user applies a radial pressure on the flexible part 20 it will move into a position covering the proximal end 7 of the needle cannula 5 as shown in FIG. 9.

Example 6

FIG. 10-11

FIGS. 10 to 11 discloses a different design. The hub 10 is on the inside surface provided with a plurality of protrusions 113 which is used to connect the needle assembly 101 to an injection device via a bayonet coupling. On the surface, the hub 110 is provided with a number of tracks 114 guiding a shield 130.

The shield 130 comprises a plate 132 which on the distal side is provided with engagement arms 134 engaging the tracks 114 such that the plate 132 is axially guided in the area of the hub 110 surrounded by the annular sleeve 112. On its proximal side the plate 132 is provided with a number of hooks 135 and in the centre of the plate an opening 137 is provided for the back needle 107.

In the initial position when the needle assembly is delivered to the user, the plate 132 is located distally in the hub 110 as disclosed in FIG. 10A. When a user connects the needle assembly 101 to an injection device, the distal end of the injection device engages the hooks 135. After performing the injection, the user removes the needle assembly 101 from the injection device, however the hooks 135 on the plate 132 engages the injection device and the plate 132 is pulled in the proximal direction. Once the hooks 135 are outside the annular sleeve 112 the can flex in the radial direction such that the engagement between the hooks 135 and the injection device can be released. In this position which is disclosed in FIG. 11B, locking arms 136 engages the hub 110 and prevents the base plate 132 from being moved in the distal direction and the back needle 107 of the needle cannula 105 is effectively covered.

Example 7

FIG. 12-13

Figure 12A:
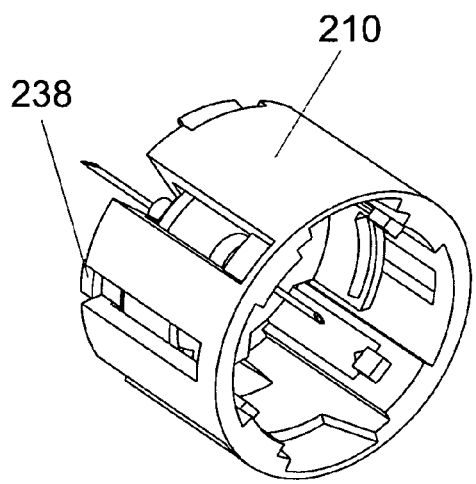
FIG. 12A-B Show a three dimensional view of an alternative back needle protection.
Figure 12B:
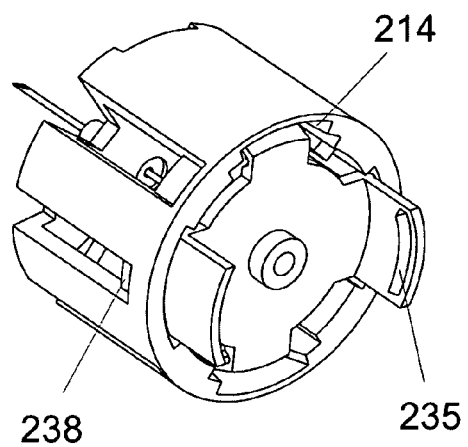
Figure 13A:
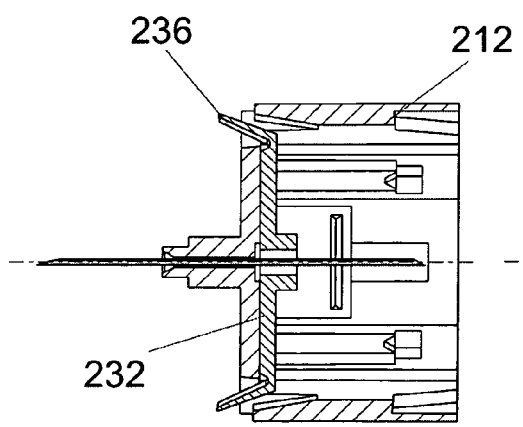
FIG. 13A-B Show a cross sectional view of the needle assembly of FIG. 12A-B.
Figure 13B:
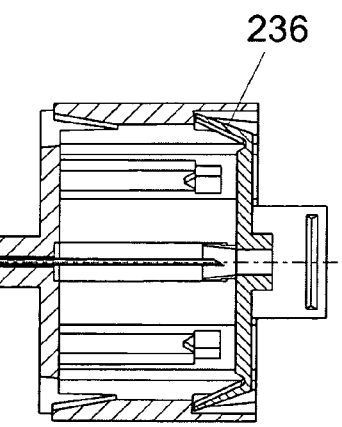

In the embodiment disclosed in the FIGS. 12-13, the track 214 guiding the plate 232 is embedded in the surface of the hub 210. Opposite the previous example, the snaps 235 engaged by the injection device and the locking arms 236 are provided in different positions on the periphery of the plate 232 thereby adding to the stability of the needle assembly. Further a locking edge 212 is provided inside the hub 210, which locking edge 212 is engaged by the locking arms 236 when the plate 232 is in the locked position i.e. the position in which the stops 238 encounters the hub 210, as disclosed in FIG. 12B.

Example 8

FIG. 14-15

In the example disclosed in FIG. 14-15, the plate 332 is provided with a locking arm 336 which slides along a curved surface 311 inside the hub 310 as the plate is pulled in the proximal direction when dismounted from the injection device. The curved surface 311 urges the plate 332 in a sideway direction. Once the plate 332 enters its locked position the stop 338 drops over a locking edge 312 in which position the opening 337 in the plate 332 is dislocated from the axis X of the needle cannula 305.

The various needle assemblies disclosed in the foregoing can be attached to any random injection device either by a thread or a bayonet coupling. Further a combined thread and bayonet coupling as described in details in EP 1.536.654, which is hereby incorporated by reference, could be used. As could a broad variety of different ways of mounting needle assemblies on an injection device be foreseen e.g. different snap or click-on connections such as snap-lock connections, snap-on/screw-off connections, luer-lock connections etc.

Where a bayonet coupling is preferred the protrusions 113 which is part of the bayonet grip could also be used as locking edges such that the locking arm 236 irreversible locks behind the protrusions 113.

Some preferred embodiments have been shown in the foregoing, but it should be stressed that the invention is not limited to these, but may be embodied in other ways within the subject matter defined in the following claims, e.g. could a needle assembly as herein described be delivered to the user in a rigid and sterile container which further could be shaped as a tool for assisting the user in mounting the needle assembly onto the injection device.

The invention claimed is:

1. A needle assembly for an injection device comprising:
    a needle cannula comprising a first elongated part with a first end and a second elongated part with a second end,
    a hub comprising a base and an annular sleeve extending from the base, the annular sleeve having structure to remove the hub from the injection device, and wherein the needle cannula is secured to the hub such that the first elongated part extends from the base in a direction away from the sleeve and the second elongated part extends in the opposite direction, the second elongated part being at least partly surrounded by the sleeve,
    wherein the needle assembly further comprises a protection structure which is axially pulled along the axial extension of the needle cannula from a first position to a second position when the hub is removed from the injection device, wherein the second position of at least a part of the protection structure is located in a position proximal of the second elongated part of the needle cannula such that a user is prevented from contacting the second end of the second elongated part of the needle cannula,
    wherein the protection structure comprises a plate which is axially guided, and
    the plate is provided with snap structure to engage the injection device.

2. A needle assembly according to claim 1, wherein the plate is guided inside the hub.

3. A needle assembly according to claim 1, wherein the plate is provided with locking structure for irreversibly locking the plate in its proximal position.

4. A needle assembly and an injection device in combination, wherein the needle assembly comprises:
    a needle cannula comprising a first elongated part with a first end and a second elongated part with a second end,
    a hub comprising a base and an annular sleeve extending from the base, the annular sleeve having structure for removably mounting the hub onto the injection device, and wherein the needle cannula is secured to the hub such that the first elongated part extends from the base in a direction away from the sleeve and the second elongated part extends in the opposite direction, the second elongated part being at least partly surrounded by the sleeve,
    wherein the needle assembly further comprises protection structure which is axially pulled along the axial extension of the needle cannula from a first position to a second position when the hub is removed from the injection device, in which the second position of at least a part of the protection structure is located in a position proximal of the second elongated part of the needle cannula such that a user is prevented from contacting the second end of the second elongated part of the needle cannula, and
    wherein the injection device comprises engaging structure engageable with the protection structure for axial movement of the protection structure,
    wherein the protection structure comprises a plate which is axially guided, and
    the plate is provided with snap structure to engage the injection device.

5. A needle assembly and an injection device in combination according to claim 4 in which the injection device is provided with a thread engageable with a snap structure provided on the protection structure.

6. A needle assembly and an injection device in combination according to claim 5 in which the protection structure is a plate provided with snap structure.

7. A needle assembly and an injection device in combination according to claim 6 in which the plate is provided with locking structure to irreversibly lock the plate in its proximal position.

8. A needle assembly and an injection device in combination according to claim 4 in which, the protection structure automatically engages with the injection device when the needle assembly is mounted on the injection device and the protection structure is automatically pulled by the injection device to a locked position during dismounting of the needle assembly from the injection device.

* * * * *